United States Patent [19]

Thygesen et al.

[11] Patent Number: 4,932,949
[45] Date of Patent: Jun. 12, 1990

[54] PANTY BRIEF FOR FIXATION OF NAPKIN PRODUCTS AND A METHOD OF MAKING SUCH PANTY BRIEFS

[75] Inventors: Eskild G. Thygesen; Johannes N. Kristensen, both of Ikast, Denmark

[73] Assignee: A/S Tytex, Denmark

[21] Appl. No.: 249,564

[22] PCT Filed: Jan. 20, 1988

[86] PCT No.: PCT/DK88/00009
§ 371 Date: Sep. 16, 1988
§ 102(e) Date: Sep. 16, 1988

[87] PCT Pub. No.: WO88/05270
PCT Pub. Date: Jul. 28, 1988

[30] Foreign Application Priority Data

Jan. 20, 1987 [DE] Fed. Rep. of Germany ....... 0312/87

[51] Int. Cl.$^5$ ............................................. A01F 13/16
[52] U.S. Cl. ..................................... 604/386; 604/393; 604/397
[58] Field of Search .............. 604/394, 395, 396, 397, 604/398, 399, 400, 401, 402, 385.2, 386, 384, 393

[56] References Cited

U.S. PATENT DOCUMENTS

| | | |
|---|---|---|
| 2,523,079 | 9/1950 | Walter et al. . |
| 2,826,199 | 3/1958 | Brandon .............................. 604/397 |
| 3,098,484 | 7/1963 | Younger ......................... 604/397 X |
| 3,509,881 | 5/1970 | Sabee ................................... 604/397 |
| 3,613,686 | 10/1971 | DeWoskin ........................... 604/396 |
| 3,656,324 | 4/1972 | Jackson . |
| 3,687,141 | 8/1972 | Matsuda .......................... 604/397 X |
| 3,714,946 | 2/1973 | Rodes .............................. 604/398 X |
| 3,882,871 | 5/1975 | Taniguchi .................... 604/385.2 X |
| 4,227,531 | 2/1980 | McLeod .......................... 604/397 X |
| 4,244,367 | 1/1981 | Rollenhagen ................... 604/397 X |
| 4,352,356 | 10/1982 | Tong ............................... 604/398 X |
| 4,813,950 | 3/1989 | Branch ................................ 604/396 |

FOREIGN PATENT DOCUMENTS

3343622 6/1985 Fed. Rep. of Germany .
2082803 12/1971 France .
2251204 9/1976 France .

Primary Examiner—Richard J. Apley
Assistant Examiner—Rachel M. Healey
Attorney, Agent, or Firm—Watson, Cole, Grindle & Watson

[57] ABSTRACT

A panty brief for holding a diaper comprises at least one holding part (10). According to the invention, the holding part is produced integrally with the front piece and/or the back piece. The holding part (10) may consist of threads (11) which are not knitted together with the remainder of the bag side (1) and which are placed symmetrically to hold a diaper symmetrically in relation to leg openings (5,6). The panty brief is made in endless lengths and is shown as it appears after the production with the wrong side turned out. Accordingly, after the production and severing the only operations required are to turn the panty brief inside out and to place the diaper in the holding part (10). Hereby, a panty brief is achieved which securely holds a diaper and which may be produced in endless lengths without the need of any afterfashioning.

12 Claims, 2 Drawing Sheets

PANTY BRIEF FOR FIXATION OF NAPKIN PRODUCTS AND A METHOD OF MAKING SUCH PANTY BRIEFS

BACKGROUND OF THE INVENTION

The present invention relates to a panty brief for holding a diaper and consisting wholly or partly of elastic textile material, preferably made by knitting or crocheting, and formed as a flat, substantially rectangular bag, the bag sides of which form a front piece and a back piece, which are closed along the marginal edge zones at the sides and along a central part of the marginal edge zones at the bottom to form a crotch region, separating two non-connected parts of the marginal edge zones at the bottom of the bag for producing leg openings, which panty brief comprises means for holding the diaper which is at least partially accomodated therein.

A panty brief, which substantially is of the above described type is known e.g. from U.S. Pat. No. 3,656,324, and the present invention is a further development of the known panty brief which makes the panty brief suitable for holding the diaper.

Panty briefs intended for holding diapers are known in different types, however, these are made as factory-tailored panty brief provided with sewed-on pockets inside the panty briefs. The diaper is placed in these pockets so as to be partly or totally contained therein. Hereby a secure holding of the diaper is obtained even when the user is physically active.

However, such panty briefs are disadvantageous, partly in that they have to be manufactured in a relatively great number of sizes and designs so as to fit diapers and persons of different individual sizes, and partly in that these panty briefs are expensive to manufacture as a great part of after-fashioning in the form of cutting, edging, seaming, etc. is required.

In an attempt to solve some of these problems and to provide cheap panty briefs it is known to manufacture the panty briefs from wholly or partly elastic material by knitting or crocheting. A possibility of holding is provided in these panty briefs by using a looser and firmer knitting in different portions of the panty brief and by knitting-in elastic threads in different portions. Accordingly, a diaper may be contained in a more loosely knitted portion, whereas the more firmly knitted portions and the elastic threads will be positioned along the edge zone of the diaper, thereby holding it.

In many situations, however, this holding of the diaper will not provide sufficient security, especially when the user is physically active, as the diaper may be displaced to a position in which it will be useless. Moreover, these panty briefs are disadvantageous when they are used by psychically handicapped persons, who may easily remove the diaper either intentionally or unintentionally.

Even though these panty briefs may be manufactured at low costs and even though they in many applications will act satisfactorily they will not give a holding of a diaper which is sufficiently secure for all applications.

So as to remedy this drawback and to provide a better holding of a diaper it has been proposed to make a panty brief, e.g. as known from DE published application No. 1,933,530, comprising holding means. These holding means are made in form of elastic ribbon-shaped material which is intended to be placed across the end portions of the diaper. However, such a construction is suitable only in conjunction with smaller diapers placed so as to extend through the crotch region, as is the case with sanitary towels. Accordingly, the panty brief as disclosed in said DE patent specification will be unsuitable for use in conjunction with larger diapers used for incontinent adults, especially if the user is physically active or if the user is a psychically handicapped person, who may remove the diaper either intentionally or unintentionally. Moreover, the known holding means are connected with the panty brief at an after-fashioning. An after-fashioning is labour consuming and accordingly, it constitutes an undesired and very great part of the production costs. Furthermore, the known holding means cannot be used in conjunction with diapers used by adult men suffering from urine incontinence.

SUMMARY OF THE INVENTION

Accordingly, it is the object of the invention to remedy the above mentioned drawbacks by providing a panty brief of the type mentioned by way of introduction, which is produced in endless lengths by automatic machines, and which is provided with holding means making it possible, without any after-fashioning, to hold a diaper in a secure way so that the diaper cannot be removed or displaced to a position in which it is useless, said holding means especially enabling the holding of diapers used by adult men suffering from urine incontinence.

According to the present invention, this object is achieved by providing the holding means in the form of at least one symmetrically placed pocket-forming holding part, produced integrally with at least one of the bag sides and extending over approximately $\frac{1}{3}$ of the height of the bag side, and which holding part, in the finished panty brief, extends adjacent and in a plane substantially parallel with the front piece and/or the back piece.

Hereby it becomes possible, in a surprisingly simple manner and using conventional equipment, to make panty briefs, in endless lengths by automatic machines, comprising holding means in the form of pocket-forming holding parts. These pocket-forming holding parts make it possible to hold a diaper in a secure way so that the diaper may not be removed or displaced to a position in which it will be useless. The extension of the pocket-forming holding part over $\frac{1}{3}$ of the height of the panty brief will ensure not only that the diaper will not be displaced but also that the diaper is not rotated during the physical activity of the user. Moreover, the pocket-forming holding part will be especially suitable in conjunction with a diaper used by adult men suffering from urine incontinence. Such a diaper is often made in a form intended to be placed at the front area of user and having a downward tapering directed towards the crotch region. A holding over a substantial part of the length of such diaper is required to avoid that the diaper rotates to a position in which it is useless.

The invention also relates to a method of making panty briefs for holding diapers and consisting wholly or partly of elastic textile material, preferably by knitting or crocheting, each panty brief being formed as a flat, substantially rectangular bag, the bag sides of which form a front piece and a back piece, which are closed along the marginal edge zones at the sides and along a central part of the marginal edge zones at the bottom, which panty brief comprises means for holding the diaper which is at least partially accomodated therein, and which panty briefs are made in endless lengths of two superposed webs, which at mutually spaced intervals are interconnected in the transverse direction of the webs for producing the bag sides, which method is characterized in that the holding means are provided in the form of at least one symmetrically placed pocket-forming holding part, that said holding part is produced integrally with at least one of the bag sides and is produced so as to extend over approximately ⅓ of the height of the bag side, and that said holding part is produced so as to extend adjacent and in a plane substantially parallel with the front piece and/or the back piece in the finished panty brief.

DESCRIPTION OF THE PREFERRED EMBODIMENTS

As explained above the present invention is a further development of a panty brief as disclosed in U.S. Pat. No. 3,656,324, the content of which hereby is incorporated by reference. Materials, knitting types, sizes, embodiments etc. which are explained in said U.S. patent in connection with the panty brief will also apply to the production of the present panty brief and in the following only the features distinguishing the present panty brief from the known panty brief will be emphasized.

The panty brief according to the invention is distinguished in that it is provided with at least one holding part for holding a diaper.

Figure 1:
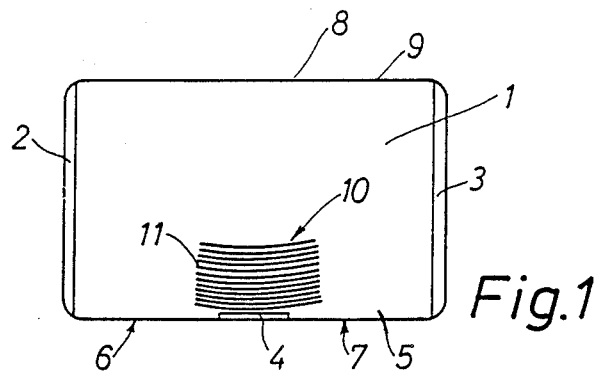
FIG. 1 is a diagrammatic side view of an embodiment of a panty brief according to the invention, seen as produced and before turning the inside out.

FIG. 1 shows a substantially rectangular bag side 1 for a panty brief. The bag side 1 shown forms a front piece of the panty brief, and the bag side is through marginal edge zones 2,3 connected with a superposed substantially identical bag side (not shown).

The bag sides are produced on conventional knitting machines and are along a central part 4 of a marginal edge zone 5 connected for producing a crotch region, leg openings 6,7 being formed at each side of the central part 4 and extending to the closed marginal edge zones 2,3. The waist opening 8 of the panty brief is provided between nonconnected marginal edge zones 9, which in a known way create an elastic waist band by means of elastic threads.

A holding part 10 is made simultaneously with the production of the bag side 1, and in the embodiment shown in FIG. 1 it is constituted by elastic threads 11, which over a part of the front piece 1 are not knitted together with the remainder of the web forming the front piece. The free threads run substantially parallel with the bottom and top marginal edge zones 7,9 of the front piece 1. The threads, which may be provided in any suitable number, extend across approximately ⅓ of the width of the front piece and over approximately ⅓ of the height of the front piece.

The elastic free threads 11, together with the part of the front piece 1 placed immediately adjacent, provide a pocket-forming holding part 10, wherein a diaper may be contained. In this embodiment the pocket-forming holding part is intended to hold a diaper used by adult men suffering from urine incontinence and the placing and the extension of the holding part provides for a free accomodation of penis in the diaper intended to be placed in the holding part 10.

Like the embodiments of the panty brief shown in FIGS. 2-5, the panty brief shown in FIG. 1 is illustrated in the form as it appears after manufacturing and severing from adjacent panty briefs. Accordingly, these Figures illustrate a panty brief with its wrong side turned outward. When the panty brief is to be used the inside is turned out, so that the holding part which after the manufacturing is placed at the outer surface of the manufactured product will be placed inside the panty brief and is ready to receive a diaper, which the panty brief is intended to hold.

Accordingly, the panty brief illustrated may be manufactured by automatic machines without the need of any after-fashioning and the only operation required for enabling the use of the panty brief is to perform said turning of the inside out so that the pocket is placed inside the panty brief; thereafter a diaper (not shown) may be placed in the holding part 10 and the panty brief is ready for use.

However, it is also possible to provide the free threads 11 on the surface facing the inside of the panty brief and it is likewise possible to interconnect the free threads for producing a web.

Figure 2:
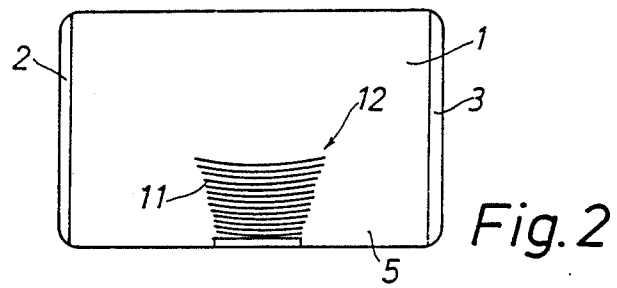
FIG. 2 is a diagrammatic side view corresponding to FIG. 1 of a further embodiment of a panty brief according to the invention.

FIG. 2 shows a panty brief substantially corresponding to the embodiment shown in FIG. 1. However, the free threads 11 are in this embodiment manufactured with a gradually decreasing extension across the width of the front piece, decreasing from the uppermost thread towards the lowermost thread, thereby producing a pocket-forming holding part 12 tapering towards the crotch region.

This panty brief is also intended for use in conjunction with the same diaper as is the embodiment shown in FIG. 1, however, the gradual tapering of the pocket-forming holding part 12 provides a secure holding of a diaper used by adult men suffering from urine incontinence. Such diapers are often manufactured in a form downwardly tapering toward that part of the diaper intended to be placed at the crotch of the user.

In FIGS. 1 and 2 only a diagrammatic view of the panty brief as seen from the front is shown as the panty brief will have a substantially flat back piece.

In case the panty brief is intended for use in conjunction with diapers used by persons suffering from urine- and faeces incontinence, the back piece of the panty brief will have a configuration substantially corresponding to the shown configuration of the front piece; free threads holding the diaper in relation to the back piece of the panty brief will be provided too.

However, a diaper of this type often has a greater extension of the part which is intended to be placed at the back side of the user's body, and accordingly, the holding part intended to be provided in the back piece often has a greater extension than the holding part intended to be used in conjunction with the front piece just as this first mentioned holding part usually has a greater extension in direction towards the waist opening of the panty brief.

It is obvious that the threads forming the holding parts may be provided in other patterns and with other sizes, depending on the size and shape of the diapers 25. Thus, it is convenient that a panty brief intended for use in conjunction with a diaper for persons suffering from urine- and faeces incontinence is manufactured with a pocket made of free threads 11, which both at the front piece and the back piece of the panty brief are provided in such a way that an upwardly tapering holding part is produced whereby the diaper hereby securely is prevented from being displaced forwards or backwards in relation to the user's body. Simultaneously, this form of the holding parts in the front piece and the back piece respectively will impede an intentional removal of the diaper, and accordingly, this embodiment will be especially suitable to be used by psychically handicapped persons.

Figure 3:
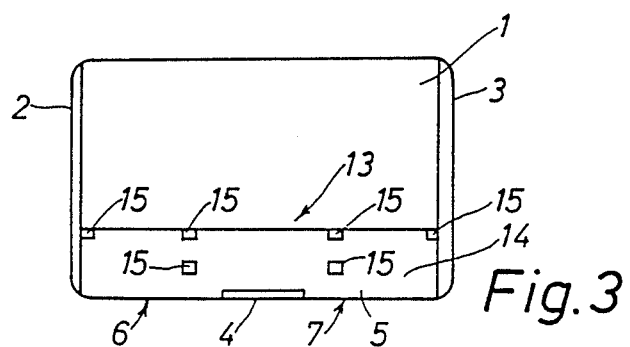
FIG. 3 is a diagrammatic side view corresponding to FIG. 1 of a further embodiment of a panty brief according to the invention.

In the embodiment of the panty brief shown in FIG. 3, the holding part 13 is constituted by a surplus web part 14 manufactured integrally with the web constituting the front piece 1. Accordingly, the panty brief is manufactured with one of the superposed webs having a greater width than the other, and during the manufacturing the surplus web part 14 of the broader web at points 15 along each marginal edge zone facing away from the front piece will be connected with elastic threads, which also are connected with the front piece 1 at points placed at a distance from the marginal edge zone 5 at the bottom of the panty brief, said distance corresponding to the width of the surplus part 14. The elastic threads draw the surplus web part 14 of the web upward in such a way that it is lying parallel with the front piece 1 and connected hereto at the spaced points 15, which superpose the corresponding points on the front piece. By a suitable placing of the points 15 a pocket-forming holding part 13 is provided in the area above the closed central part 4 of the marginal edge zones 5 at the bottom of the panty brief.

Figure 4:
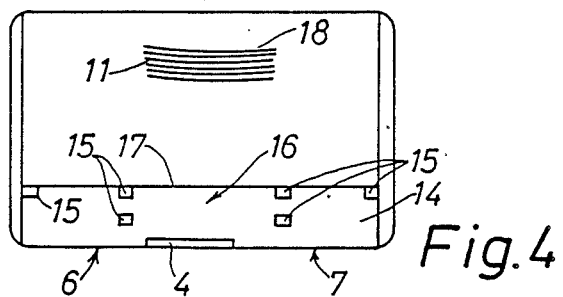
FIG. 4 is a diagrammatic side view corresponding to FIG. 1 of a further embodiment of a panty brief according to the invention.

The embodiment shown in FIG. 4 is made substantially in the same way as the embodiment shown in FIG. 3 in that a surplus part 14 of the web used for making the front piece 1 of the panty brief at points 15 and by means of elastic threads is positioned adjacent and parallel with the front piece for providing a pocket-forming holding part 16 substantially corresponding to the holding part 13.

According to this embodiment a further holding part 18 is provided between the upper edge 17 of the surplus part and the marginal edge zone 9 at the waist opening, said further holding part 18 being made by means of free threads. This further holding part 18 is placed with a relatively small extension in direction of the height of the panty brief and together with the web of the front piece 1 it forms an annular holding part. The free threads 11 will preferably extend across approximately ⅓ of the width of the front piece, however this extension may be adapted to the diaper used. As in the above mentioned embodiments, the free threads are elastic and will exert a pressure against the diaper for holding it between the threads and the web of the front piece.

The further holding part 18 will provide a more secure holding of the diaper than the holding obtained with the pocket-forming holding part alone, seeing that the further holding part 18 will hold the diaper immediately below the waist band, and simultaneously, the holding part 16 holds the diaper substantially in the user's crotch region. With this mutual separated placing of the two holding parts the diaper may not be displaced or rotated laterally even when the user is physically active, and due to the fact that the holding part 16 will be closed at the marginal edge zone 4 a bottom is formed in the pocket preventing a backward displacement of the diaper through the user's crotch region. The further holding part 18 will exert a pressure against the diaper, which from the opposite side is affected by the pressure exerted by the elastic waist band in direction of the body and the diaper provided therebetween, and accordingly, a displacement upward along the body of the user is also prevented.

Figure 5:
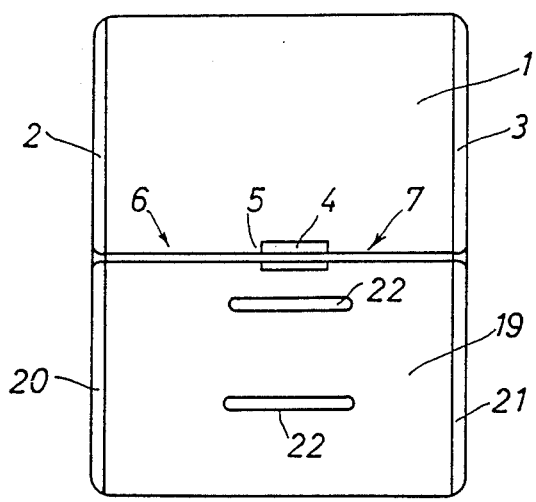
FIG. 5 is a diagrammatic side view corresponding to FIG. 1 of a further embodiment of a panty brief according to the invention.

In the embodiment shown in FIG. 5 the holding part is provided by two further superposed webs which are manufactured integrally with the superposed webs constituting the panty brief itself. Accordingly, the part 19 of the further webs, which is manufactured integrally with the front piece 1, will be connected thereto along the marginal edge zone 5, a connection being provided between the two further superposed webs along the central part 4 of the marginal edge zones 5 to provide the leg openings 6 and 7, in the same way as in the above described embodiments. The further webs are closed along marginal edge zones 20,21 in the sides, and when the further webs are turned into the space between the front piece 1 and the back piece of the panty brief, a double layered panty brief is provided. Accordingly, the part 19 will be placed adjacent the front piece, whereas the not shown superposed part will be provided adjacent the not shown back piece of the panty brief. In the further part 19 intended to be placed at the front side of the user, openings 22 are provided. The openings 22 run substantially parallel with the bottom of the panty brief and extend approximately across ⅓ of the width of the panty brief. The openings are provided in a number and with a mutual placing depending of the diaper to be used in conjunction with the panty brief. In the embodiment shown, two openings 22 are provided running parallel at different distances from the bottom of the panty brief. Said openings are intended to hold a diaper used by adult men suffering from urine incontinence. The diaper is placed so that the lowermost portion adjacent the crotch region is inserted into the space between the front piece 1 and the part 19, and in the same way the uppermost portion of the diaper is inserted through an opening 22, so that this part is also placed in the space between the front piece 1 and the part 19. Hereby the central portion of the diaper is placed inside the double layered panty brief and a free accomodation of penis in the diaper is possible.

In case a double layered embodiment is to be used in conjunction with diapers for persons suffering from urine- and faeces incontinence, openings corresponding to the openings 22 will be provided in the further part (not shown), which is superposed on the further part 19 so that is possible to hold the diaper both at the front side and the back side.

Figure 6:
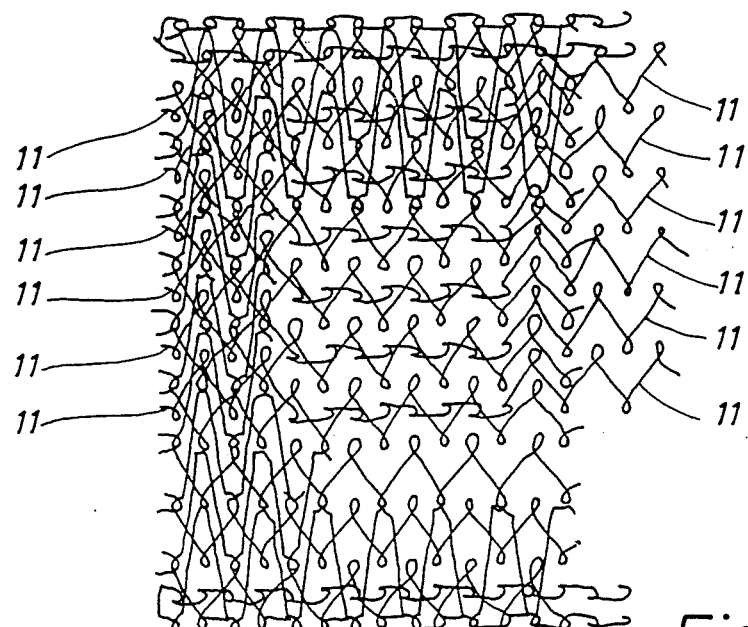
FIG. 6 is a fragmentary representation of a knitting pattern illustrating how the free threads are made.

For representing of a knitting mode FIG. 6 shows a knitting pattern illustrating how the free threads 11 are made. This Figure is an example only illustrating the manufacturing of the free threads and the number of threads shown is not limiting for the invention.

A panty brief as described above is made in the form of endless lengths of two superposed webs, which at mutually spaced intervals are interconnected in the transverse direction of the webs. The transverse connections are used to sever the panty briefs and they provide the closed marginal edge zones 2 and 3 respectively for the panty briefs; accordingly, during the manufacturing one marginal edge zone 2 for one panty brief will be manufactured consecutive with a marginal edge zone 3 for an adjacent panty brief. By the severing through the transverse connections, each individual panty brief is made in the form of a flat substantially rectangular bag the bag sides of which form a front piece 1 and a back piece. During the manufacturing the marginal edge zones 5 are closed at mutually spaced intervals, viz. at the central parts 4 for producing of the leg openings 5,6. At least in conjunction with one of the bag sides an integral holding part 10,12,13,16,18 is manufactured; said holding part runs adjacent and in a plane substantially parallel with one of the bag sides in the finished panty brief. The holding parts are made substantially symmetrical in relation to a symmetry plan passing through the front piece 1 and the back piece so that a diaper later placed in this holding part will be placed symmetrically in relation to the leg openings, and accordingly, in relation to the body of the user.

According to a specific embodiment of the method the holding part is manufactured so that the front piece 1 is made of a web with a greater width producing a surplus web part 14 which does not superpose the web used for the back piece. The surplus part 14 is at points along the marginal edge zone through elastic treads connected with points provided at a distance from the bottom of the bag side; said distance corresponds to the width of the surplus part 14 of the web, and accordingly, this surplus part will be drawn upward to lie adjacent and parallel with the front piece 1 due to the elasticity of the threads. Between the connection points 15 a holding part 13 is formed. According to a further method the holding part is made by threads 11 extending over approximately ⅓ of the length of a bag side; said threads are not knitted together with the remainder of the web forming the bag side so that a holding part for containing a diaper is formed between the free threads 11 and the web itself. According to an alternative method a combination of free threads 11 and a surplus part 14 drawn up to lie parallel with the bagside may be used.

The panty brief shown in FIG. 5 is made by manufacturing two further webs 19, integrally with each of the bag sides, said further webs each having a size substantial identical with the size of a bag side. The further webs 19 are closed along the marginal edge zones 20,21. When the further webs are turned into the space between the front piece 1 and the back piece a double layered panty brief is formed. During the manufacturing of the further webs, openings 22 are produced in at least one of these further webs and after having turned the inside out, a diaper may be held in this panty brief by inserting the ends of the diaper through the openings 22 to be placed in the space between the two layers of the double layered panty brief.

By these methods it becomes possible, by means of conventional equipment normally used to knit two superposed layer, to manufacture a final product containing one or several pockets, and which accordingly fullfils the same function as a panty brief manufactured with more than two superposed layers for providing pockets or holding parts, wherein a diaper may be contained.

We claim:

1. A panty brief for holding a diaper and consisting wholly or partly of elastic textile material, and formed as a flat, substantially rectangular bag, the bag sides of which are webs forming a front piece and a back piece, which are closed along marginal edge zones at the sides and along a central part of marginal edge zones at the bottom to form a crotch region, separating two nonconnected parts of the marginal edge zones at the bottom of the bag for producing leg openings, which panty brief comprises means for holding the diaper which is at least partially accommodated therein, characterized in that the holding means are provided in the form of at least one symmetrically placed pocket-forming holding part, produced integrally with at least one of the bag sides and extending over approximately ⅓ of the height of the bag side, and which holding part, in the finished panty brief, extends adjacent and in a plane substantially parallel with the front piece and/or the back piece.

2. A panty brief according to claim 1, characterized in that the holding part is constituted by elastic free threads, which over a part of the front piece are not knitted together with the remainder of the web providing the front piece, which elastic free threads run substantially parallel with the bottom and top of the front piece and extend approximately across ⅓ of the width of the front piece.

3. A panty brief according to claim 2, characterized in that the free threads in a direction from the top of the front piece towards the bottom have a gradually decreasing extension across the width of the front piece whereby the threads together with the front piece itself produce a pocket tapering towards the crotch region.

4. A panty brief according to claim 1, characterized in that the holding part is constituted by a web manufactured integrally with the front piece, the front piece being manufactured from a web having a greater width than the web providing the back piece, that the part of the web constituting the additionel width is connected, at spaced points along the marginal edge zone facing away from the front piece with elastic threads which also are knitted together with the front piece at points placed at a distance from the marginal edge zone of the front piece along the bottom of the panty brief so that the elastic threads draw the surplus part of the web upward to lie parallel with the front piece and connected thereto at said spaced points, thus forming a pocket at the central part of the front piece.

5. A panty brief according to claim 4, characterized in that the holding part furthermore comprises elastic free threads which over a part of the front piece are not knitted together with the remainder of the web providing the front piece, these threads provided at a distance from the upper edge of the pocket provided by means of the additional width of the web.

6. A panty brief according to claim 2, characterized in that a corresponding holding part is provided in the back piece.

7. A panty brief according to claim 1, characterized in that the holding part is constituted by two further webs, which along the marginal edge zones at the bottom of the panty brief are manufactured integrally with the front piece and the back piece respectively, each of said further webs having substantially same size as the front piece and back piece and being closed along marginal edge zones in the sides, so that a double layered panty brief is provided when the further webs are turned into the space between the front piece and the back piece of the panty brief, and that mutually spaced-apart openings are provided at least in the further web which is intended to be placed at the front side of the user, which openings run substantially parallel with the bottom of the panty brief and extend approximately across ⅓ of the width of the panty brief.

8. A panty brief according to claim 1, characterized in that the holding part is provided in the surface of the front piece and/or the back piece facing against the user when using the panty brief.

9. A method of making panty briefs for holding diapers and consisting wholly or partly of elastic textile material, each panty brief being formed as a flat, substantially rectangular bag, the bag sides of which form a front piece and a back piece, which are closed along the marginal edge zones at the sides and along a central part of the marginal edge zones at the bottom, which panty brief comprises means for holding the diaper which at least partially is accomodated therein, and which panty briefs are made in endless lengths of two superposed webs, which at mutually spaced intervals are interconnected in the transverse direction of the webs for producing the bag sides, which method is characterized in that the holding means are provided in the form of at least one symmetrically placed pocket-forming holding part, that said holding part is produced integrally with at least one of the bag sides and is produced so as to extend over approximately ⅓ of the height of the bag-side, and that said holding part is produced so as to extend adjacent and in a plane substantially parallel with the front piece and/or the back piece in the finished panty brief.

10. A method according to claim 9, characterized in that one of the bag sides is produced from a web with a greater width than the web for the other bag side, and that the surplus part is along the marginal edge zone facing away from the bag side, at points mutually spaced in the longitudinal direction, through elastic threads knitted together with points on the bag side and at a distance from the bottom thereof, which distance corresponds to the width of the surplus part of the web, whereby the holding part is formed.

11. A panty brief according to claim 9, characterized in that the holding part is produced wholly or partly from elastic threads which over approximately ⅓ of the length of the bag side, are not knitted together with the remainder of the web constituting the bag side.

12. A method according to claim 9, characterized in that the holding part is produced from two further webs, each having a size substantially corresponding to the size of a bag side, said webs being made integrally with each of the bag sides along the marginal edge zones at the bottom of the bag, that the further webs are closed along the marginal edge zones at the sides, that mutually spaced-apart openings are provided at least in one of the further webs, which openings run substantial parallel with the bottom of the panty brief and in different distances therefrom, and that the further webs are turned inside the panty brief for producing a double layered panty brief.

* * * * *

UNITED STATES PATENT AND TRADEMARK OFFICE
CERTIFICATE OF CORRECTION

PATENT NO. : 4,932,949
DATED : June 12, 1990
INVENTOR(S) : Eskild G. THYGESEN et al.

It is certified that error appears in the above-identified patent and that said Letters Patent is hereby corrected as shown below:

On the title page, column 1, item (30), change "Jan. 20, 1987 (DE) Fed. Rep. of Germany .... 0 312/87" to read --Jan. 20, 1987 (DK) Denmark .... 0312/87--.

Signed and Sealed this

First Day of October, 1991

*Attest:*

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,932,949

DATED : June 12, 1990

INVENTOR(S) : Eskild Georg Thygesen, Johannes Nyvang Kristensen

It is certified that error appears in the above-identified patent and that said Letters Patent is hereby corrected as shown below:

The title page should be deleted to appear as per attached title page.

Fig. 1, should be deleted to appear as Fig. 1 as shown on the attached page.

Signed and Sealed this

Twenty-second Day of September, 1992

Attest:

DOUGLAS B. COMER

Attesting Officer

Acting Commissioner of Patents and Trademarks

United States Patent

Thygesen et al.

[11] Patent Number: 4,932,949
[45] Date of Patent: Jun. 12, 1990

[54] PANTY BRIEF FOR FIXATION OF NAPKIN PRODUCTS AND A METHOD OF MAKING SUCH PANTY BRIEFS

[75] Inventors: Eskild G. Thygesen; Johannes N. Kristensen, both of Ikast, Denmark

[73] Assignee: A/S Tytex, Denmark

[21] Appl. No.: 249,564

[22] PCT Filed: Jan. 20, 1988

[86] PCT No.: PCT/DK88/00009

§ 371 Date: Sep. 16, 1988

§ 102(e) Date: Sep. 16, 1988

[87] PCT Pub. No.: WO88/05270

PCT Pub. Date: Jul. 28, 1988

[30] Foreign Application Priority Data

Jan. 20, 1987 [DE] Fed. Rep. of Germany ....... 0312/87

[51] Int. Cl.$^5$ .............................................. A01F 13/16
[52] U.S. Cl. .................................... 604/386; 604/393; 604/397
[58] Field of Search ................. 604/394, 395, 396, 397, 604/398, 399, 400, 401, 402, 385.2, 386, 384, 393

[56] References Cited

U.S. PATENT DOCUMENTS

| | | |
|---|---|---|
| 2,523,079 | 9/1950 | Walter et al. |
| 2,826,199 | 3/1958 | Brandon ............................ 604/397 |
| 3,098,484 | 7/1963 | Younger ........................ 604/397 X |
| 3,509,881 | 5/1970 | Sabee ................................ 604/397 |
| 3,613,686 | 10/1971 | DeWoskin ........................ 604/396 |
| 3,656,324 | 4/1972 | Jackson. |
| 3,687,141 | 8/1972 | Matsuda ...................... 604/397 X |
| 3,714,946 | 2/1973 | Rodas ........................... 604/398 X |
| 3,882,871 | 5/1975 | Taniguchi .................. 604/385.2 X |
| 4,227,531 | 2/1980 | McLeod ......................... 604/397 X |
| 4,244,367 | 1/1981 | Rollenhagen ................ 604/397 X |
| 4,352,356 | 10/1982 | Tong ............................ 604/398 X |
| 4,813,950 | 3/1989 | Branch ............................. 604/396 |

FOREIGN PATENT DOCUMENTS

| | | |
|---|---|---|
| 3343622 | 6/1985 | Fed. Rep. of Germany. |
| 2082803 | 12/1971 | France. |
| 2251204 | 9/1976 | France. |

Primary Examiner—Richard J. Apley
Assistant Examiner—Rachel M. Healey
Attorney, Agent, or Firm—Watson, Cole, Grindle & Watson

[57] ABSTRACT

A panty brief for holding a diaper comprises at least one holding part (10). According to the invention, the holding part is produced integrally with the front piece and/or the back piece. The holding part (10) may consist of threads (11) which are not knitted together with the remainder of the bag side (1) and which are placed symmetrically to hold a diaper symmetrically in relation to leg openings (5,6). The panty brief is made in endless lengths and is shown as it appears after the production with the wrong side turned out. Accordingly, after the production and severing the only operations required are to turn the panty brief inside out and to place the diaper in the holding part (10). Hereby, a panty brief is achieved which securely holds a diaper and which may be produced in endless lengths without the need of any afterfashioning.

12 Claims, 2 Drawing Sheets

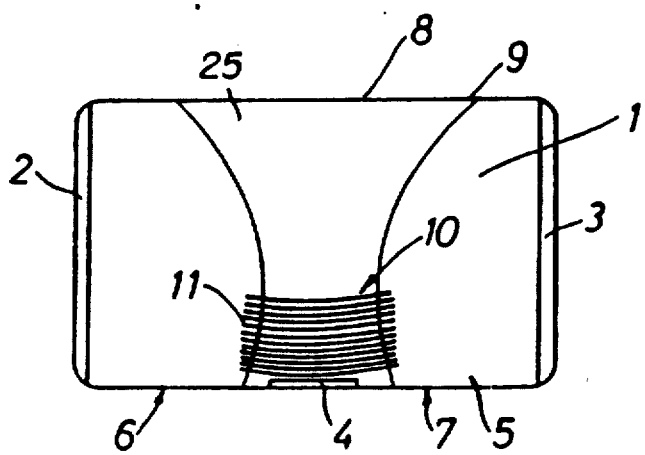

UNITED STATES PATENT AND TRADEMARK OFFICE
CERTIFICATE OF CORRECTION

PATENT NO. : 4,932,949

DATED : June 12, 1990

INVENTOR(S) : Eskild Georg Thygesen, Johannes Nyvang Kristensen

It is certified that error appears in the above-identified patent and that said Letters Patent is hereby corrected as shown below:

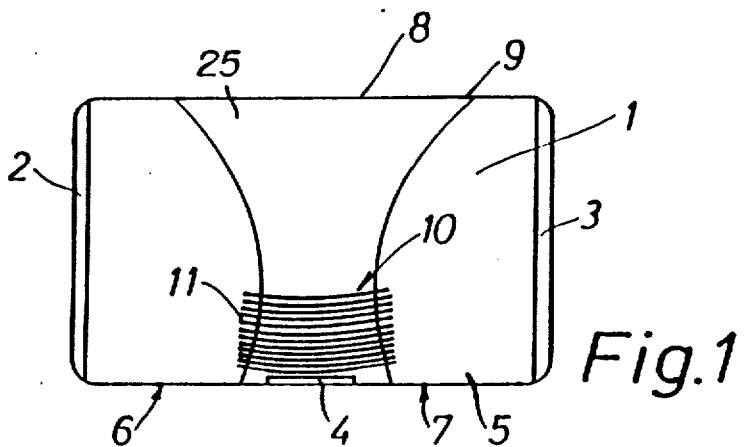

Fig.1